(12) United States Patent
Liao et al.

(10) Patent No.: US 8,912,197 B2
(45) Date of Patent: Dec. 16, 2014

(54) CRYSTALLINE FORM OF CARBAMOYL-CYCLOHEXANE DERIVATIVES

(71) Applicant: Forest Laboratories Holdings Ltd., Hamilton (BM)

(72) Inventors: Xiangmin Liao, Commack, NY (US); Hiajian (Jim) Zhu, Smithtown, NY (US); Andreas Grill, Hauppauge, NY (US)

(*) Notice: Subject to any disclaimer, the term of this patent is extended or adjusted under 35 U.S.C. 154(b) by 0 days.

(21) Appl. No.: 13/827,294

(22) Filed: Mar. 14, 2013

(65) Prior Publication Data

US 2014/0051710 A1 Feb. 20, 2014

Related U.S. Application Data

(60) Provisional application No. 61/684,903, filed on Aug. 20, 2012.

(51) Int. Cl.
*A61K 31/4965* (2006.01)
*C07D 295/00* (2006.01)
*C07D 295/135* (2006.01)
*C07C 51/00* (2006.01)
*C07C 57/15* (2006.01)

(52) U.S. Cl.
CPC ......... *C07D 295/135* (2013.01); *C07B 2200/13* (2013.01); *C07C 51/00* (2013.01); *C07C 57/15* (2013.01)
USPC ..................................... 514/255.03; 544/393

(58) Field of Classification Search
CPC .... C07B 2200/13; C07C 51/00; C07C 57/15; C07D 241/04
USPC ...................................... 544/393; 514/255.03
See application file for complete search history.

(56) References Cited

U.S. PATENT DOCUMENTS

| | | |
|---|---|---|
| 6,528,529 B1 | 3/2003 | Brann et al. |
| 6,566,550 B2 | 5/2003 | Lowe, III et al. |
| 7,737,142 B2 | 6/2010 | Csongor et al. |
| 7,829,569 B2 | 11/2010 | Liao et al. |
| 7,943,621 B2 | 5/2011 | Czibula et al. |
| 2003/0144285 A1 | 7/2003 | Brann et al. |
| 2006/0229297 A1 | 10/2006 | Csongor et al. |
| 2007/0099931 A1 | 5/2007 | Ghosh et al. |
| 2007/0244093 A1 | 10/2007 | Boehm et al. |
| 2007/0259885 A1 | 11/2007 | Bathe et al. |
| 2009/0036468 A1 | 2/2009 | Samoriski et al. |
| 2009/0275597 A1 | 11/2009 | Papadakis et al. |
| 2010/0016334 A1 | 1/2010 | Sarkar et al. |
| 2010/0137335 A1 | 6/2010 | Csongor et al. |
| 2010/0197666 A1 | 8/2010 | Laszlovsky et al. |
| 2010/0197704 A1 | 8/2010 | Laszlovsky et al. |
| 2011/0015208 A1 | 1/2011 | Samoriski et al. |
| 2011/0028722 A1 | 2/2011 | Liao et al. |
| 2012/0028991 A1 | 2/2012 | Samoriski et al. |
| 2012/0046302 A1 | 2/2012 | Papadakis et al. |
| 2013/0040966 A1 | 2/2013 | Sarkar et al. |

FOREIGN PATENT DOCUMENTS

| | | |
|---|---|---|
| WO | WO97/11070 | 3/1997 |
| WO | WO99/50247 | 10/1999 |
| WO | WO99/67206 | 12/1999 |
| WO | WO01/05763 | 1/2001 |
| WO | WO03-029233 | 4/2003 |
| WO | WO2005/012266 | 2/2005 |
| WO | WO2006/034774 | 4/2006 |
| WO | WO2007/033191 | 3/2007 |
| WO | WO2008/139235 | 11/2008 |
| WO | WO2008/142461 | 11/2008 |
| WO | WO2008/142462 | 11/2008 |
| WO | WO2008/142463 | 11/2008 |
| WO | WO2010/009309 | 1/2009 |
| WO | WO2009/020897 | 2/2009 |
| WO | WO2010/126527 | 11/2010 |

OTHER PUBLICATIONS

Glase et al.; "4-Bromo-1-Methoxy-N-[2-(4-Aryl-1-Piperazinyl)Ethyl]-2-Naphthalenecarboxamides: Selective Dopamine D3 Receptor Partial Agonists"; Bioorganic & Medicinal Chemistry Letters, vol. 6, No. 12, pp. 1361-1366, Jun. 18, 1996.
Belliotti et al., "Novel Cyclohexyl Amides as Potent and Selective D3 Dopamine Receptor Ligands," Bioorg. Med. Chem. Lett. 1997, 7, 18, 2403-2408.
Levant, "The D3 Dopamine Receptor: Neurobiology and Potential Clinical Relevance," Pharmacol. Rev. 1997, 49, 231-252.
Levant et al., "Dopamine D3 Receptors: Relvance for the Drug Treatment of Parkinson's Disease," CNS Drugs 1999, 12, 391-402.
Levant et al., "D3 dopamine receptors in rat spinal cord: implications for sensory and motor function," Neurosci. Lett. 2001, 303, 9-12.
Pilla et al., "Selective inhibition of cocaine-seeking behavior by a partial dopamine D3 receptor agonist," Nature 1999, 400, 371-375.
Schwartz et al., "Dopamine D3 Receptor: Basic and Clinical Aspects," Clin. Neuropharmacol. 1993, 16, 295-314.
Sokoloff et al., "Molecular cloning and characterization of a novel dopamine receptor (D3) as a target for neuroleptics," Nature, 1990, 347, 146-151.
Wong et al., "Schizophrenia: from phenomenology to neurobiology," Neurosci. Biobehav. Rev. 2003, 27, 269-306.
Berge, et al., "Pharmaceutical Salts", J. Pharm. Sciences (1977).
Gurevich et al., "Mesolimbic Dopamine D3 Receptors and Use of Antipsychotics in Patients with Schizophrenia, A Postmortem Study", Archives of General Psychiatry, 54, 225-232, 1997. Abstract.
Laszlovsky et al., "Dopamine D2/D3 Receptor Occupancy of RGH-188, a D3/D2 Antagonist/Partial Agonist Antipsychotic, in Healthy Volunteers", 20th Congress of the European College of Neuropsychopharmacology, Vienna Austria, Oct. 13-17, 2007.

(Continued)

Primary Examiner — Kendra D Carter

(57) ABSTRACT

The present invention relates to novel crystalline forms of carbamoyl-cyclohexane derivatives and, more particularly, to novel co-crystalline forms of trans-1{4-[2-[4-(2,3-dichlorophenyl-piperazin-1-yl]-ethyl]-cyclohexyl}-3,3-dimethyl urea hydrochloride and an acid such as fumaric acid. Processes for preparing these forms, compositions containing these forms, and methods of use thereof are also described.

12 Claims, 5 Drawing Sheets

(56) References Cited

OTHER PUBLICATIONS

Abstracts of Papers, 234th ACS National Meeting, Boston, MA, United States, Aug. 19-23, 2007, MEDI-383.
International Search Report for International Application No. PCT/HU2004/00056, mailed Nov. 9, 2004.
International Search Report for International Application No. PCT/HU2008/000044, mailed Jan. 29, 2009.
International Search Report for International Application No. PCT/US2008/063181, mailed Aug. 15, 2008.
International Search Report for International Application No. PCT/US2009/050835, mailed Sep. 10, 2009.
International Search Report for International Application No. PCT/HU2008/000046, mailed Sep. 22, 2008.
International Search Report for International Application No. PCT/HU2008/000051, mailed Sep. 12, 2008.
International Search Report for International Application No. PCT/HU2008/000052, mailed Feb. 3, 2009.
International Search Report for International Application No. PCT/US2008/072066, mailed Oct. 20, 2008.
International Search Report for International Application No. PCT/US2009/42460, mailed Jul. 29, 2009.

CRYSTALLINE FORM OF CARBAMOYL-CYCLOHEXANE DERIVATIVES

CROSS-REFERENCE TO RELATED APPLICATIONS

This application claims priority under 35 U.S.C. §119 to U.S. Provisional Application No. 61/684,903, filed on Aug. 20, 2012, the contents of which are incorporated herein by reference.

Each of the applications and patents cited in this text, as well as each document or reference cited in each of the applications and patents (including during the prosecution of each issued patent; "application cited documents"), and each of the U.S. and foreign applications or patents corresponding to and/or claiming priority from any of these applications and patents, and each of the documents cited or referenced in each of the application cited documents, are hereby expressly incorporated herein by reference. More generally, documents or references are cited in this text, either in a Reference List before the claims, or in the text itself; and, each of these documents or references ("herein-cited references"), as well as each document or reference cited in each of the herein-cited references (including any manufacturer's specifications, instructions, etc.), is hereby expressly incorporated herein by reference. Documents incorporated by reference into this text may be employed in the practice of the invention.

FIELD OF THE INVENTION

The present invention relates to novel crystalline forms of carbamoyl-cyclohexane derivatives and, more particularly, to novel co-crystalline forms of trans-1{4-[2-[4-(2,3-dichlorophenyl)-piperazin-1-yl]-ethyl]-cyclohexyl}-3,3-dimethyl urea hydrochloride and an acid. Processes for preparing these forms, compositions containing these forms, and methods of use thereof are also described.

BACKGROUND OF THE INVENTION

International Patent Application Publication No. WO 2005/012266 discloses carbamoyl-cyclohexane derivatives that are $D_3$ and $D_2$ dopamine receptor subtype preferring ligands. WO 2005/012266 discloses that trans-1{4-[2-[4-(2,3-dichlorophenyl)-piperazin-1-yl]-ethyl]-cyclohexyl)}-3,3-dimethyl-urea has a binding affinity for dopamine $D_3$ receptors ($IC_{50}$ between 1 and 10 nM) and a binding affinity for dopamine $D_2$ receptors ($IC_{50}$ between 10 and 50 nM). Thus, trans-1{4-[2-[4-(2,3-dichlorophenyl)-piperazin-1-yl]-ethyl]-cyclohexyl}-3,3-dimethyl-urea may be used as a mixed dopamine $D_3/D_2$ receptor ligand for use in the treatment of disorders which require modulation of dopamine receptor(s).

One particular carbamoyl-cyclohexane derivative disclosed in Hungarian Patent Application No. P0700339 and U.S. Pat. No. 7,737,142 is trans-4-{2-[4-(2,3-dichlorophenyl)-piperazin-1-yl]-ethyl}-N,N-dimethylcarbamoyl-cyclohexylamine hydrochloride, which is also known as trans-1{4-[2-[4-(2,3-dichlorophenyl)-piperazin-1-yl]-ethyl]-cyclohexyl}-3,3-dimethyl-urea hydrochloride, or cariprazine, the structural formula for which is shown below in figure (I).

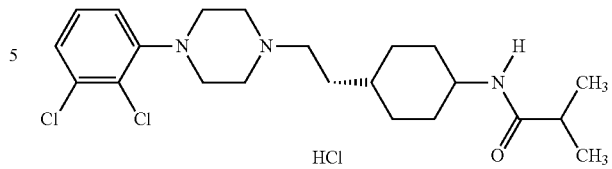

(I)

Hungarian Patent Application No. P0700339 also discloses processes for preparing trans-1{4-[2-[4-(2,3-dichlorophenyl)-piperazin-1-yl]-ethyl]-cyclohexyl}-3,3-dimethyl-urea hydrochloride, and describes a crystalline form of trans-1{4-[2-[4-(2,3-dichlorophenyl)-piperazin-1-yl]-ethyl]-cyclohexyl}-3,3-dimethyl-urea hydrochloride, which will be referred to hereinafter as polymorph "Form I". The crystalline hydrochloride salt of polymorph Form I is disclosed in U.S. Pat. No. 7,943,621, as well as solvates and hydrates thereof.

U.S. Pat. No. 7,829,569 discloses processes for preparing trans-1{4-[2-[4-(2,3-dichlorophenyl)-piperazin-1-yl]-ethyl]-cyclohexyl}-3,3-dimethyl-urea hydrochloride, and describes a crystalline form of trans-1{4-[2-[4-(2,3-dichlorophenyl)-piperazin-1-yl]-ethyl]-cyclohexyl}-3,3-dimethyl-urea hydrochloride, which will be referred to hereinafter as polymorph "Form III".

Pharmaceutical co-crystals are crystalline molecular complexes that contain the drug substance along with an additional molecule present in the same crystal structure. The additional molecule or guest has been described in the literature as a co-crystal former. Co-crystalline forms show different physicochemical properties compared to the drug substance alone, including melting point, chemical reactivity, apparent solubility, dissolution rate, optical and mechanical properties, vapor pressure, and density. These properties can have a direct effect on the ability to process and/or manufacture a drug substance and the corresponding finalized dosage forms, as well as an effect on drug product stability, dissolution, and bioavailability. Co-crystallization has also been used to isolate or purify a drug substance during manufacturing.

Co-crystal formation and the properties of co-crystalline forms cannot be predicted on the basis of known properties of the drug substance and the co-crystal former. Disclosed herein are novel co-crystals of trans-1{4-[2-[4-(2,3-dichlorophenyl)-piperazin-1-yl]-ethyl]-cyclohexyl}-3,3-dimethyl-urea hydrochloride and an acid, e.g., fumaric acid and oxalic acid.

SUMMARY OF THE INVENTION

The present invention relates to novel crystalline forms of carbamoyl-cyclohexane derivatives and, more particularly, to novel co-crystalline forms of trans-1{4-[2-[4-(2,3-dichlorophenyl)-piperazin-1-yl]-ethyl]-cyclohexyl}-3,3-dimethyl urea hydrochloride and a co-crystal former, such as acids like fumaric acid. Processes for preparing these forms, compositions containing these forms, and methods of use thereof are also described.

In one embodiment, a co-crystal of the present invention has an X-ray powder diffraction pattern comprising characteristic peaks at about 8.3 and about 38.5±0.2 degrees 2θ.

In other embodiments, the co-crystal has an X-ray powder diffraction pattern comprising characteristic peaks at about 8.3, about 36.5, about 38.5 and about 39.5±0.2 degrees 2θ.

In yet another embodiment, the co-crystal has a melting endotherm at about 170° C. as determined by differential scanning calorimetry and a characteristic peak at about 8.3±0.2 degrees 2θ in an X-ray powder diffraction pattern.

In another aspect, the present invention relates to a process for preparing a co-crystal comprising:
(i) combining trans-1{4-[2-[4-(2,3-dichlorophenyl)piperazin-1-yl]-ethyl]-cyclohexyl}-3,3-dimethyl urea hydrochloride, an acid, and an organic solvent to form a mixture, and
(ii) grinding the mixture.

In one embodiment, the trans-1{4-[2-[4-(2,3-dichlorophenyl)-piperazin-1-yl]-ethyl]-cyclohexyl}-3,3-dimethyl urea hydrochloride and the acid are present in a 1:1 ratio.

In another embodiment, the acid is fumaric acid.

In another embodiment, the organic solvent is selected from the group consisting of tetrahydrofuran, methanol, acetonitrile, ethyl acetate, acetone, chloroform, and a mixture thereof.

In yet another aspect, the present invention relates to a process for preparing the co-crystal comprising:
(i) adding trans-1{4-[2-[4-(2,3-dichlorophenyl)-piperazin-1-yl]-ethyl]-cyclohexyl}-3,3-dimethyl urea hydrochloride and an acid, to an organic solvent to form a mixture, and
(ii) evaporating the organic solvent.

In one embodiment, step (ii) comprises evaporating the organic solvent at ambient pressure and temperature.

In another aspect, the present invention relates to a co-crystal obtained or obtainable by a process comprising:
(i) combining trans-1{4-[2-[4-(2,3-dichlorophenyl)-piperazin-1-yl]-ethyl]-cyclohexyl}-3,3-dimethyl urea hydrochloride, an acid, and an organic solvent to form a mixture, and
(ii) grinding the mixture.

In another aspect, the present invention relates to a co-crystal obtained or obtainable by a process comprising:
(i) adding trans-1{4-[2-[4-(2,3-dichlorophenyl)-piperazin-1-yl]-ethyl]-cyclohexyl}-3,3-dimethyl urea hydrochloride and an acid to an organic solvent to form a mixture, and
(ii) evaporating the organic solvent.

In another aspect, pharmaceutical compositions comprising the co-crystals of the present invention are provided.

In yet another aspect, the present invention relates to a method for treating a condition which requires modulation of dopamine receptors comprising administering to a patient in need thereof an effective amount of a co-crystal as disclosed herein. In one embodiment, the dopamine receptor is a dopamine $D_3$ receptor and/or a dopamine $D_2$ receptor. In another embodiment, the condition is selected from the group consisting of schizophrenia, schizo-affective disorders, cognitive impairment accompanying schizophrenia, mild-to-moderate cognitive deficits, dementia, psychotic states associated with dementia, psychotic depression, mania, acute mania, bipolar disorder, bipolar depression, major depressive disorder, paranoid and delusional disorders, dyskinetic disorders, neuroleptic induced parkinsonism, depression, anxiety and drug abuse.

These and other embodiments are disclosed or are obvious from and encompassed by the following detailed description.

BRIEF DESCRIPTION OF THE FIGURES

The following Detailed Description, given by way of example, but not intended to limit the invention to specific embodiments described, may be understood in conjunction with the accompanying Figures, incorporated herein by reference, in which.

DETAILED DESCRIPTION OF THE INVENTION

Figure 1:
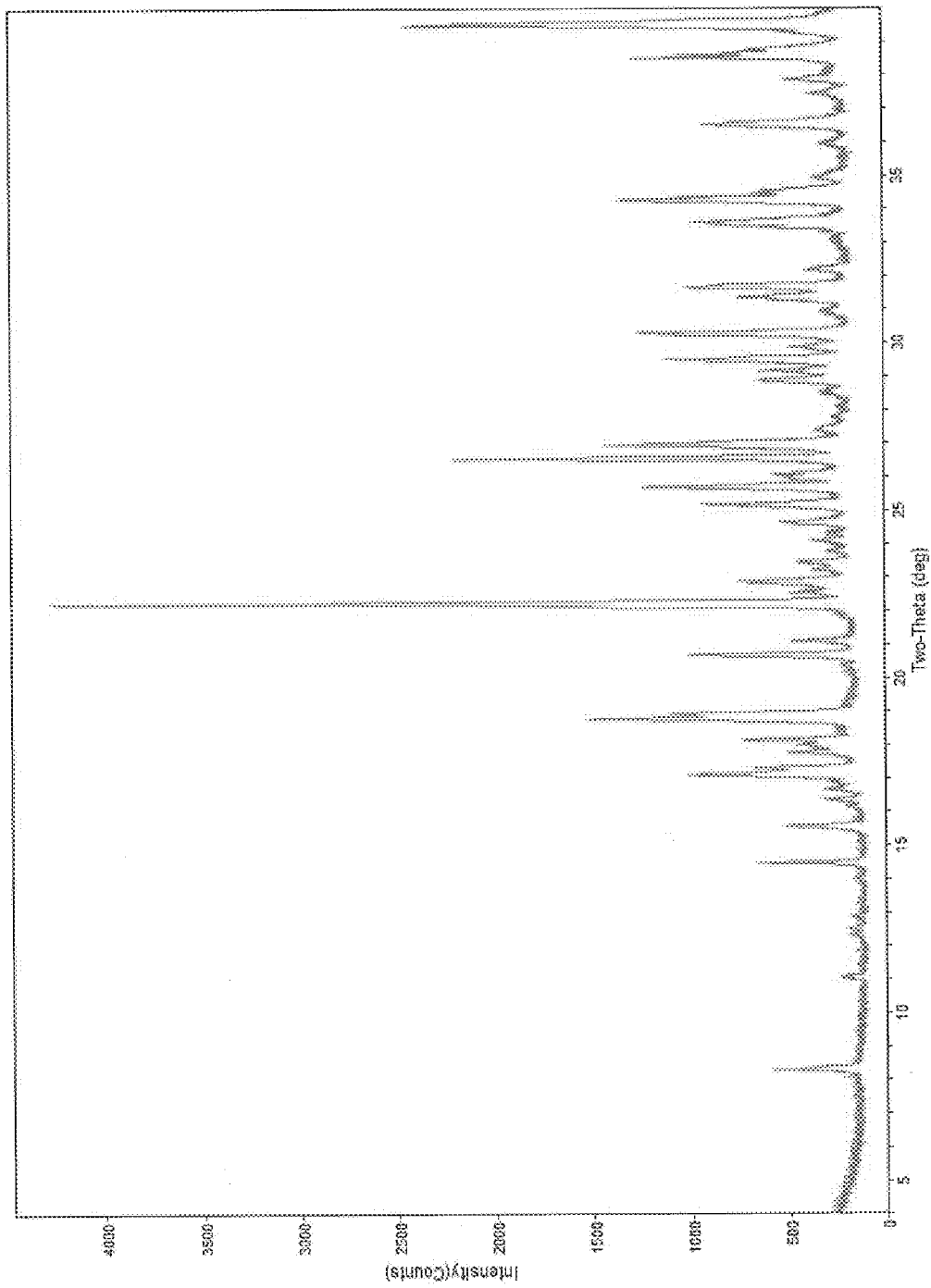
FIG. 1 shows the X-ray powder diffraction pattern of a co-crystal of trans-1{4-[2-[4-(2,3-dichlorophenyl)-piperazin-1-yl]-ethyl]-cyclohexyl}-3,3-dimethyl urea hydrochloride and fumaric acid.

Unless otherwise defined, all technical and scientific terms used herein have the same meaning as commonly understood by one of ordinary skill in the art to which this invention pertains. Methods and materials similar or equivalent to those described herein can be used in the practice of the present invention, and exemplified suitable methods and materials are described below. For example, methods may be described which comprise more than two steps. In such methods, not all steps may be required to achieve a defined goal and the invention envisions the use of isolated steps to achieve these discrete goals. In addition, the materials, methods, and examples are illustrative only and not intended to be limiting.

The present invention relates to solid state physical properties of trans-1{4-[2-[4-(2,3-dichlorophenyl)-piperazin-1-yl]-ethyl]-cyclohexyl}-3,3-dimethyl-urea hydrochloride. These properties may be influenced by controlling the conditions under which this compound is obtained in solid form. Solid state physical properties include, for example, the flowability of the milled solid. Flowability affects the ease with which the material is handled during processing into a pharmaceutical product. When particles of the powdered compound do not flow past each other easily, a formulation specialist must take that fact into account in developing a tablet or capsule formulation, which may necessitate the use of glidants such as colloidal silicon dioxide, talc, starch or tribasic calcium phosphate.

Another important solid state property of a pharmaceutical compound is its rate of dissolution in aqueous fluid. The rate of dissolution of an active ingredient in a patient's stomach fluid may have therapeutic consequences since it imposes an upper limit on the rate at which an orally-administered active ingredient may reach the patient's bloodstream. The rate of dissolution is also a consideration in formulating syrups, elixirs and other liquid medicaments. The solid state form of a compound may also affect its behavior on compaction and its storage stability.

These practical physical characteristics are influenced by the conformation and orientation of molecules in the unit cell, which defines a particular polymorphic form of a substance. The polymorphic form may give rise to thermal behavior different from that of the amorphous material or another polymorphic form. Thermal behavior is measured in the laboratory by such techniques as capillary melting point, thermogravimetric analysis (TGA) and differential scanning calorimetry (DSC) and may be used to distinguish some polymorphic forms from others. A particular polymorphic form may also give rise to distinct spectroscopic properties that may be detectable by powder X-ray powder diffractometry (XRPD), solid state nuclear magnetic resonance (NMR) spectrometry, Raman spectroscopy and infrared (IR) spectrometry.

In deciding which polymorph is preferable, the numerous properties of the polymorphs must be compared and the preferred polymorph chosen based on the many physical property variables. It is entirely possible that one polymorph can be preferable in some circumstances in which certain aspects, such as case of preparation, stability, etc., are deemed to be critical. In other situations, a different polymorph may be preferred for greater solubility and/or superior pharmacokinetics.

The discovery of new polymorphic forms and solvates of a pharmaceutically useful compound provides a new opportunity to improve the performance characteristics of a pharmaceutical product. It enhances the repertoire of materials that a formulation scientist has available for designing, for example, a pharmaceutical dosage form of a drug with a targeted release profile or other desired characteristic.

The provision of drug substances in co-crystalline forms can offer an alternative approach to modify or control the physicochemical properties of a drug substance. Pharmaceutical co-crystals are crystalline molecular complexes that contain the drug substance along with an additional molecule present in the same crystal structure. The additional molecule or guest has been described in the literature as a co-crystal former. A co-crystal can thus be seen to be a multiple component crystal in which the drug substance and the co-crystal former are arranged in a three dimensional repetitive structure, wherein non-covalent and non-ion pair interactions exist between the drug substance and the co-crystal former, such as hydrogen bonding, pi-stacking, and van der Waals interactions. Co-crystalline forms show different physicochemical properties compared to the drug substance alone, including melting point, chemical reactivity, apparent solubility, dissolution rate, optical and mechanical properties, vapor pressure, and density. These properties can have a direct effect on the ability to process and/or manufacture a drug substance and the corresponding finalized dosage forms, as well as an effect on drug product stability, dissolution, and bioavailability. Thus co-crystallization can affect the quality, safety, and efficacy of a drug substance. It can offer an alternative to the conversion into the amorphous state with its associated problems or to the conversion into salt forms, which in a number of instances do not offer the desired physicochemical properties. Co-crystallization can also be used to isolate or purify a drug substance during manufacturing.

Exemplary co-crystal formers may include acids such as, but not limited to, inorganic acids such as hydrochloric acid, hydrobromic acid, sulfuric acid, nitric acid, and phosphoric acid, and organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartatic acid, oxalic acid, citric acid, benzoic acid, o-(4-hydroxybenzoyl) benzoic acid, cinnamic acid, madelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutaric acid, hydroxynaphthoic acid, salicylic acid, stearic acid, and muconic acid.

In particular, the present invention relates to novel crystalline forms of carbamoyl-cyclohexane derivatives and, more particularly, to novel co-crystalline forms of trans-1{4-[2-[4-(2,3-dichlorophenyl)-piperazin-1-yl]-ethyl]-cyclohexyl}-3,3-dimethyl urea hydrochloride and a co-crystal former, such as an acid like fumaric acid, and which can be identified by one or more analytical methods. The X-ray powder diffraction ("XRPD") pattern of the co-crystal of trans-1{4-[2-[4-(2,3-dichlorophenyl)-piperazin-1-yl]-ethyl]-cyclohexyl}-3,3-dimethyl urea hydrochloride and fumaric acid is provided in FIG. 1.

In certain embodiments, the present invention provides a co-crystalline form of trans-1{4-[2-[4-(2,3-dichlorophenyl)-piperazin-1-yl]-ethyl]-cyclohexyl}-3,3-dimethyl urea hydrochloride and fumaric acid characterized by a XRPD pattern having characteristic peaks at about 8.3, about 36.5, about 38.5 and about 39.5±0.2 degrees 2θ. In further embodiments, the XRPD pattern comprises at least one, for example, at least two, at least three or at least four characteristic peaks selected from about 8.3, about 36.5, about 38.5 and about 39.5±0.2 degrees 2θ.

In other embodiments, the co-crystal of trans-1{4-[2-[4-(2,3-dichlorophenyl)-piperazin-1-yl]ethyl]-cyclohexyl}-3,3-dimethyl urea hydrochloride and fumaric acid is characterized by a XRPD pattern substantially as shown in FIG. 1.

With respect to the term "substantially," one of ordinary skill in the art would understand that the relative intensities of the peaks obtained by the spectroscopic techniques described herein can vary, depending upon the sample preparation technique, the sample mounting procedure and the particular instrument employed. Moreover, instrument variation and other factors can affect 2θ values. Therefore, XRPD peak assignments can vary by plus or minus about 0.2 degrees 2θ. For infrared and Raman spectroscopy, peak assignments may vary by about plus or minus 4 $cm^{-1}$.

Figure 2:
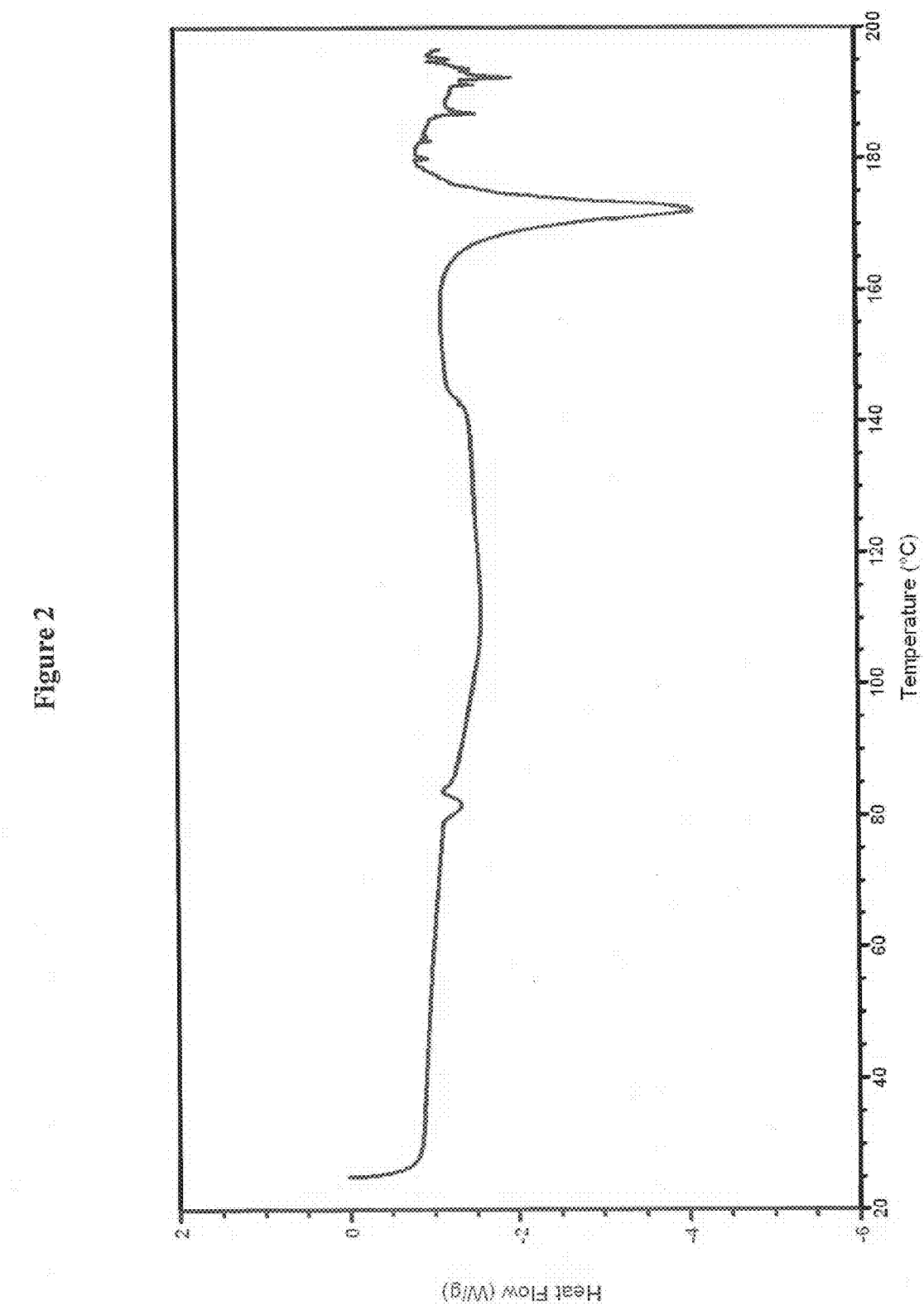
FIG. 2 shows the differential scanning calorimetry trace for a co-crystal of trans-1{4-[2-[4-(2,3-dichlorophenyl)-piperazin-1-yl]-ethyl]-cyclohexyl}-3,3-dimethyl urea hydrochloride and fumaric acid.

In another embodiment, the co-crystal of trans-1{4-[2-[4-(2,3-dichlorophenyl)-piperazin-1-yl]-ethyl]-cyclohexyl}-3,3-dimethyl urea hydrochloride and fumaric acid can also be identified by its characteristic differential scanning calorimetry ("DSC") trace, such as shown in FIG. 2. In a further embodiment, the co-crystal of trans-1{4-[2-[4-(2,3-dichlorophenyl)-piperazin 1-yl]-ethyl]-cyclohexyl}-3,3-dimethyl urea hydrochloride and fumaric acid is characterized by a DSC trace showing a melting endotherm at about 170° C.

Figure 3:
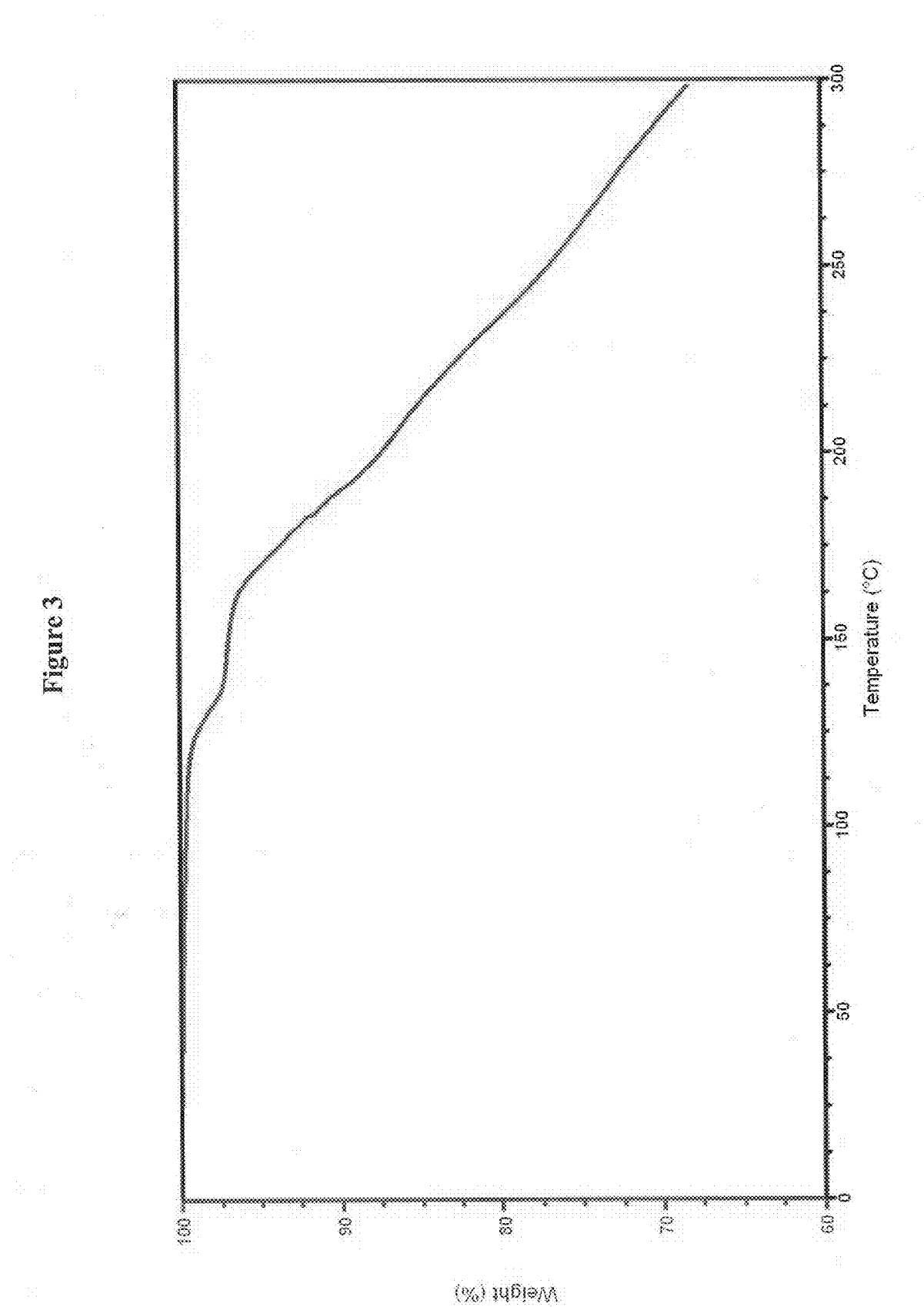
FIG. 3 shows the thermogravimetric analysis for a co-crystal of trans-1{4-[2-[4-(2,3-dichlorophenyl)-piperazin-1-yl]-ethyl]-cyclohexyl}-3,3-dimethyl urea hydrochloride and fumaric acid.

The thermogravimetric analysis ("TGA") trace for the co-crystal of trans-1{4-[2-[4-(2,3-dichlorophenyl)piperazin-1-yl]-ethyl]-cyclohexyl}-3,3-dimethyl urea hydrochloride and fumaric acid is shown in FIG. 3.

Figure 4:
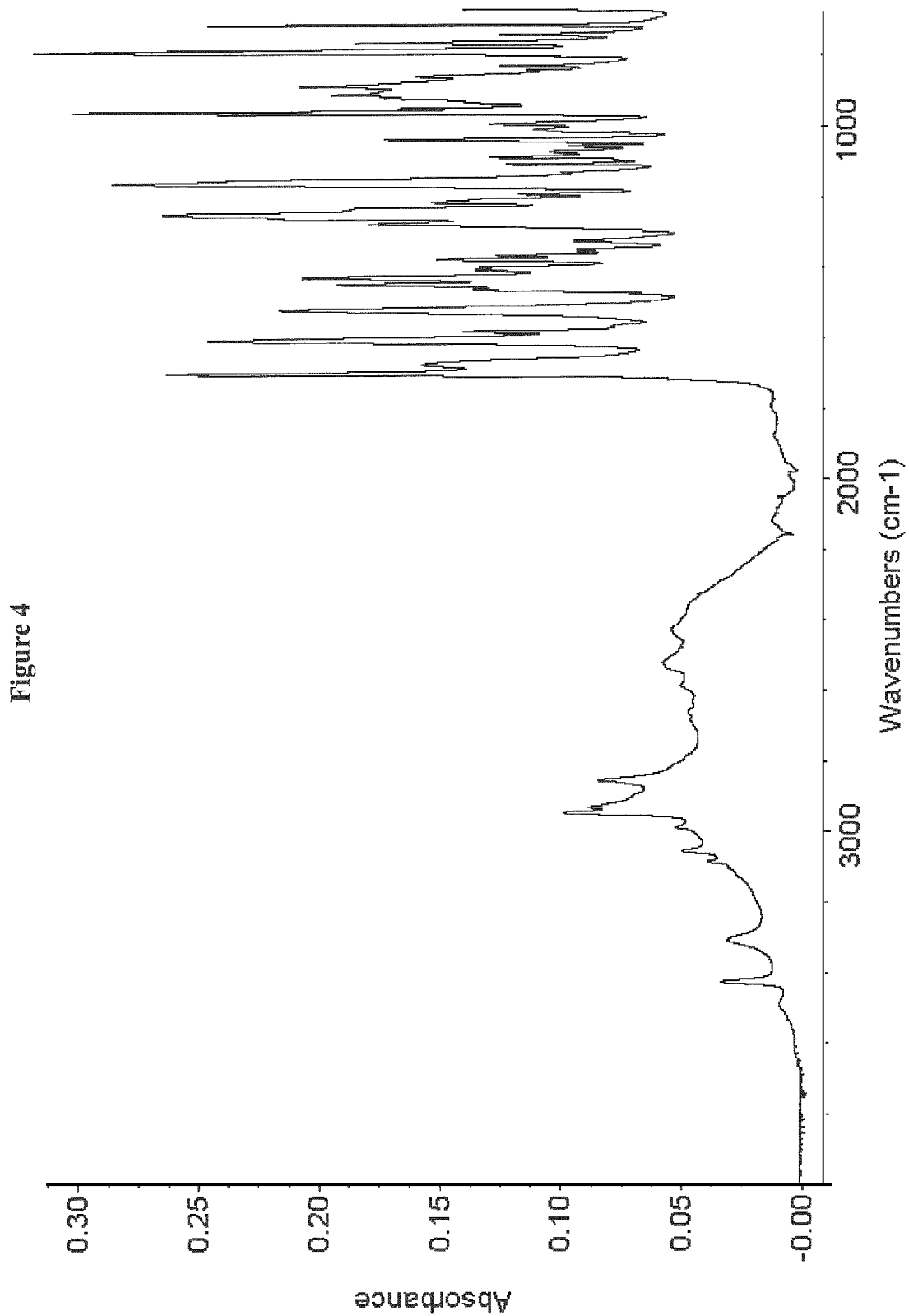
FIG. 4 shows the FTIR spectrum of a co-crystal of trans-1{4-[2-[4-(2,3-dichlorophenyl)-piperazin-1-yl]-ethyl]-cyclohexyl}-3,3-dimethyl urea hydrochloride and fumaric acid.

The co-crystal of trans-1{4-[2-[4-(2,3-dichlorophenyl)-piperazin-1-yl]-ethyl]-cyclohexyl}-3,3-dimethyl urea hydrochloride and fumaric acid can also be identified by its FTIR spectrum, which is shown in FIG. 4.

Figure 5:
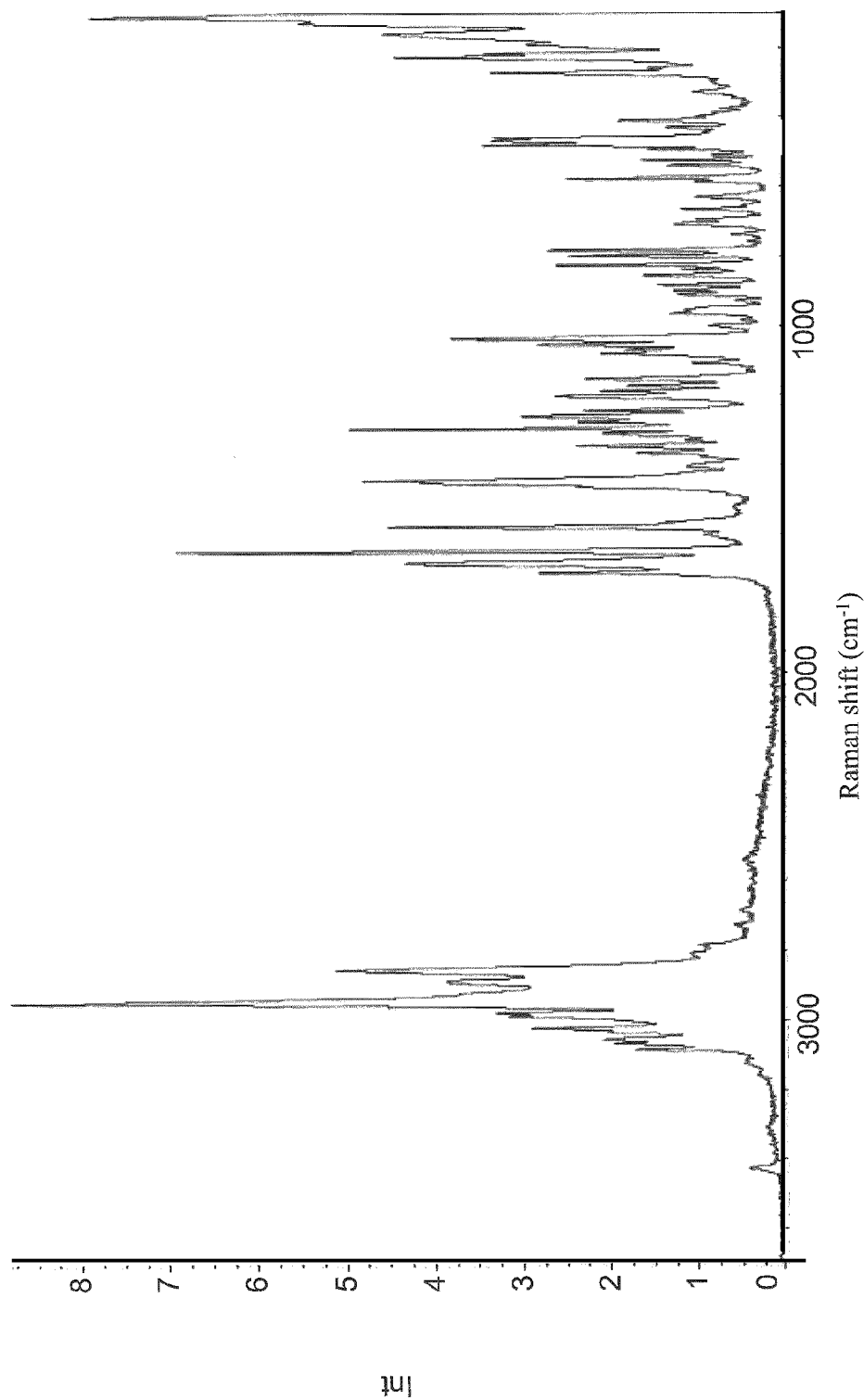
FIG. 5 shows the FT Raman spectrum of a co-crystal of trans-1{4-[2-[4-(2,3-dichlorophenyl)piperazin-1-yl]-ethyl]-cyclohexyl}-3,3-dimethyl urea hydrochloride and fumaric acid.

The co-crystal of trans-1{4-[2-[4-(2,3-dichlorophenyl)-piperazin-1-yl]-ethyl]-cyclohexyl}-3,3-dimethyl urea hydrochloride and fumaric acid can also be identified by its FT Raman spectrum, which is shown in FIG. 5.

The present invention also provides processes for preparing co-crystalline forms of trans-1{4-[2-[4-(2,3-dichlorophenyl)-piperazin-1-yl]-ethyl]-cyclohexyl}-3,3-dimethyl urea hydrochloride and an acid such as fumaric acid.

In one embodiment, co-crystalline trans-1{4-[2-[4-(2,3-dichlorophenyl)-piperazin-1-yl]-ethyl]-cyclohexyl}-3,3-dimethyl urea hydrochloride and an acid is prepared by mixing trans-1{4-[2-[4-(2,3-dichlorophenyl)-piperazin-1-yl]- ethyl]-cyclohexyl}-3,3-dimethyl urea hydrochloride and the acid. In one embodiment, the ratio of trans-1{4-[2-[4-(2,3-dichlorophenyl)-piperazin-1-yl]-ethyl]-cyclohexyl}-3,3-dimethyl urea hydrochloride and the acid is about 1:1. In another embodiment, an equimolar amount of trans-1{4-[2-[4-(2,3-dichlorophenyl)-piperazin-1-yl]-ethyl]-cyclohexyl}-3,3-dimethyl urea hydrochloride and the acid is mixed.

In another embodiment, a mixture of trans-1{4-[2-[4-(2,3-dichlorophenyl)-piperazin-1-yl]-ethyl]-cylohexyl}-3,3-dimethyl urea hydrochloride and an acid is combined in the presence of a suitable organic solvent, such as tetrahydrofuran, methanol, acetonitrile ethyl acetate, acetone, chloroform or a mixture thereof.

In another embodiment, the mixture of trans-1{4-[2-[4-(2,3-dichlorophenyl)-piperazin-1-yl]-ethyl]-cyclohexyl}-3,3-dimethyl urea hydrochloride and an acid is dissolved in an organic solvent.

In yet another embodiment, the mixture of trans-1{4-[2-[4-(2,3-dichlorophenyl)-piperazin-1-yl]-ethyl]-cyclohexyl}-3,3-dimethyl urea hydrochloride and an acid is mechanically ground.

Recrystallization may occur by any of numerous routine methods in the art, such as by cooling or evaporating the solvent to induce precipitation. In one embodiment, after dissolution, crystallization may be carried out at room (ambient) temperature, or at a temperature between about −10° C. to about 10° C. In another embodiment, crystals are obtained from a super saturated solution at room temperature.

The co-crystalline forms may be dried. For example, drying can be carried out at atmospheric (or ambient) pressure, e.g., by allowing the solvent to evaporate, or at reduced pressure (below 1 atmosphere), e.g., below about 100 Hg. For example, drying is carried out at atmospheric pressure and room temperature.

Compositions and Dosage Forms

The co-crystals of the invention can be administered alone or as an active ingredient of a formulation. Thus, the present invention also includes pharmaceutical compositions of the co-crystals of the invention, containing, for example, one or more pharmaceutically acceptable carriers. The mode of administration and dosage forms are closely related to the therapeutic amounts of the compounds or formulations which are desirable and efficacious for the given treatment application.

To prepare such pharmaceutical dosage forms, the active ingredient, is typically mixed with a pharmaceutical carrier according to conventional pharmaceutical compounding techniques. The carrier may take a wide variety of forms depending on the form of preparation desired for administration. Numerous standard references are available that describe procedures for preparing various formulations suitable for administering the compounds according to the invention. Examples of potential formulations and preparations are contained, for example, in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Arthur Osol, editor), 1553-1593 (current edition).

Administration of the co-crystals of the present invention may be accomplished according to patient needs, for example, oral, nasal, parenteral (subcutaneous, intravenous, intramuscular, intrasternal, spinal, intrathecal, intra-articular, intra-arterial, and by infusion), sub-lingual, mucosal, by inhalation, rectal, vaginal, topical, transdermal, sub-arachnoid, bronchial, lymphatic, intra-uterine, by ocular or ophthalmic administration, and other dosage forms for systemic delivery of active ingredients. Formulations suitable for oral administration are preferred (e.g., tablets, capsules).

Various solid oral dosage forms can be used for administering the co-crystals of the invention including such solid forms as tablets, gelcaps, capsules, caplets, granules, lozenges and bulk powders. The co-crystals of the present invention can be administered alone or combined with various pharmaceutically acceptable carriers, diluents (such as sucrose, mannitol, lactose, starches) and excipients known in the art, including but not limited to suspending agents, solubilizers, buffering agents, pH modifiers, thickening agents, glidants, fillers, binders, disintegrants, preservatives, colorants, flavorants, lubricants and the like. Modified release dosage forms, e.g., capsules, tablets and gels, can also advantageous in administering the compounds of the present invention.

Various liquid oral dosage forms can also be used for administering the co-crystals of the inventions, including aqueous and non-aqueous solutions, emulsions, suspensions, syrups, and elixirs. Such dosage forms can also contain suitable inert diluents known in the art such as water, glycols, oils, alcohols, and suitable carriers, additives, and excipients known in the art such as preservatives, wetting agents, sweeteners, coloring agents, flavorants, as well as agents for emulsifying and/or suspending the compounds of the invention.

For solid oral preparations such as, for example, powders, capsules, cachets, lozenges, and tablets, each comprising a predetermined amount of the active ingredient as a powder or granules. Suitable carriers and additives include starches, sugars, diluents, granulating agents, lubricants, binders, disintegrating agents and the like. Suitable carriers and additives include, for example, sucrose, mannitol, polyethylene glycol, hydroxypropyl cellulose, hydroxypropyl methyl cellulose, sodium lauryl sulphate, chremophor, Tweens, Spans, Pluronics, microcrystalline cellulose, calcium phosphate, talc, fumed silica, hydroxypropyl methyl cellulose, wax, and fatty acids, etc.

A tablet may be made by compression or molding, or wet granulation, optionally with one or more accessory ingredients. Compressed tablets may be prepared by compressing in a suitable machine, with the active compound being in a free-flowing form such as a powder or granules which optionally is mixed with, for example, a binder, disintegrant, lubricant, inert diluent, surface active agent, or discharging agent. Molded tablets comprised of a mixture of the powdered active compound with a suitable carrier may be made by molding in a suitable machine.

A syrup may be made by adding the active compound to a concentrated aqueous solution of a sugar, for example sucrose, to which may also be added any accessory ingredient(s). Such accessory ingredient(s) may include flavorings, suitable preservative, agents to retard crystallization of the sugar, and agents to increase the solubility of any other ingredient, such as a polyhydroxy alcohol, for example glycerol or sorbitol.

In some applications, it may be advantageous to utilize the active agent in a "vectorized" form, such as by encapsulation of the active agent in a liposome or other encapsulant medium, or by fixation of the active agent e.g., by covalent bonding, chelation, or associative coordination, on a suitable biomolecule, such as those selected from proteins, lipoproteins, glycoproteins, and polysaccharides.

Formulations suitable for parenteral administration usually comprise a sterile aqueous preparation of the active compound, which preferably is isotonic with the blood of the recipient (e.g., physiological saline solution). Such formulations may include stabilizing agents, suspending agents, thickening agents, ingredients that aid solubility or for preservation, liposomes or other microparticulate systems and which are designed to target the compound to blood components or one or more organs. The formulations may be presented in unit-dose or multi-dose form.

Parenteral administration may comprise any suitable form of systemic delivery or delivery directly to the CNS. Administration may for example be intravenous, intra-arterial intrathecal, intramuscular, subcutaneous, intramuscular, intra-abdominal (e.g., intraperitoneal), etc., and may be effected by infusion pumps (external or implantable) or any other suitable means appropriate to the desired administration modality.

Suppositories for rectal administration containing the co-crystals of the present invention can be prepared by mixing the compound with a suitable excipient, such as cocoa butter, hydrogenated fats, hydrogenated fatty carboxylic acids, salicylates, polyethylene glycols and the like. Formulations for vaginal administration can be in the form of a pessary, tampon, cream, gel, past foam, or spray formula containing, in addition to the active ingredient, such suitable carriers as are known in the art.

For topical administration, pharmaceutical compositions containing the co-crystals of the present invention can be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches. Transdermal formulations may be prepared by incorporating the active agent in a thixotropic or gelatinous carrier such as a cellulosic medium, e.g., methyl cellulose or hydroxyethyl cellulose, with the resulting formulation then being packed in a transdermal device adapted to be secured in dermal contact with the skin of a wearer.

Nasal and other mucosal spray or aerosol formulations (e.g. inhalable forms) can comprise purified aqueous solutions of the active compounds with preservative agents and isotonic agents. Such formulations are preferably adjusted to a pH and isotonic state compatible with the nasal or other mucous membranes. Alternatively, they can be in the form of micronized or finely divided solid powders suspended in a gas carrier. Such formulations may be delivered by any suitable means or method, e.g., by nebulizer, atomizer, metered dose inhaler, or the like.

In addition to the aforementioned ingredients, formulations of this invention may further include one or more accessory ingredient(s) selected from diluents, buffers, flavoring agents, binders, disintegrants, surface active agents, thickeners, lubricants, preservatives (including antioxidants), and the like.

In one embodiment, the invention provides a composition containing co-crystalline trans-1{4-[2-[4-(2,3-dichlorophenyl-piperazin-1-yl]-ethyl]-cyclohexyl}-3,3-dimethyl urea hydrochloride and fumaric acid.

In another embodiment, the invention provides a composition containing Form I trans-1{4-[2-[4-(2,3-dichlorophenyl)-piperazin-1-yl]-ethyl]-cyclohexyl}-3,3-dimethyl-urea hydrochloride and co-crystalline trans-1{4-[2-[4-(2,3-dichlorophenyl)-piperazin-1-yl]-ethyl]-cyclohexyl}-3,3-dimethyl urea hydrochloride and fumaric acid.

In another embodiment, the invention provides a composition containing Form III trans-1{4-[2-[4-(2,3-dichlorophenyl)-piperazin-1-yl]-ethyl]-cyclohexyl}-3,3-dimethyl-urea hydrochloride and co-crystalline trans-1{4-[2-[4-(2,3-dichlorophenyl)-piperazin-1-yl]-ethyl]-cyclohexyl}-3,3-dimethyl urea hydrochloride and fumaric acid.

Dosages

The co-crystals of the present invention can normally be administered in a daily dosage regimen (for an adult patient) of, for example, an oral dose between 1 mg and 500 mg, such as between 10 mg and 400 mg, e.g., between 10 mg and 250 mg or an intravenous, subcutaneous, or intramuscular dose of between 0.1 mg and 100 mg, such as between 0.1 mg and 50 mg, e.g., between 1 and 25 mg of the compound of present invention.

In certain embodiments, the active ingredient is administered in an amount of about 0.05 mg, about 0.1 mg, about 0.2 mg, about 0.3 mg, about 0.4 mg, about 0.5 mg, about 1 mg, about 1.5 mg, about 2 mg, about 2.5 mg, about 3 mg, about 3.5 mg, about 4 mg, about 4.5 mg, about 5 mg, about 5.5 mg, about 6 mg, about 6.5 mg, about 7 mg, about 7.5 mg, about 8 mg, about 8.5 mg, about 9 mg, about 9.5 mg, about 10 mg, about 10.5 mg, about 11 mg, about 11.5 mg, about 12 mg, about 12.5 mg or about 15 mg. In some embodiments, the active ingredient is administered in an amount of about 1.5 mg, about 3 mg, about 4.5 mg, about 6 mg, about 7.5 mg or about 9 mg. In other embodiments, the active ingredient is administered in an amount of about 1.5 mg, about 3 mg or about 4.5 mg. In yet other embodiments, the active ingredient is administered in an amount of about 3 mg, about 4.5 mg, about 6 mg, about 7.5 mg, about 9 mg, about 10.5 mg or about 12 mg. In yet other embodiments, the active ingredient is administered in an amount which ranges between any two of these dosage amounts. For example, the active ingredient is administered in an amount ranging from about 0.5 mg to about 12 mg, from about 1.5 mg to about 9 mg, from about 3 mg to about 12 mg, or from about 1.5 mg to about 4.5 mg.

The compounds of the present invention can be administered 1 to 4 times per day, for example, once a day, twice a day. The compounds of the present invention can suitably be administered for a period of continuous therapy, for example for days, weeks, months, years, or more.

Methods of Treatment

The invention also provides the use of the co-crystals of the present invention in the manufacture of a medicament for the treatment of conditions which require modulation of a dopamine receptor, e.g., a dopamine $D_3$ and/or $D_2$ receptor.

The present invention further provides methods for treating a condition which requires modulation of a dopamine receptor, e.g., a dopamine $D_3$ and/or a $D_2$ receptor. In further embodiments, the present invention provides methods for treating a condition which requires modulation of a dopamine $D_3$ and/or a $D_2$ receptor utilizing the co-crystal of the present invention.

Dysfunction of the dopaminergic neurotransmitter system is involved in the pathology of several neuropsychiatric and neurodegenerative disorders, such as schizophrenia, drug abuse and Parkinson's disease, respectively. The effect of dopamine is mediated via at least five distinct dopamine receptors belonging to the $D_1$-($D_1$, $D_5$) or the $D_2$-($D_2$, $D_3$, $D_4$) families. $D_3$ receptors have been shown to have characteristic distribution in the cerebral dopaminergic systems. Namely, high densities were found in certain limbic structures, such as nucleus accumbens and islands of Calleja. Therefore, preferential targeting of the $D_3$ receptors may be a promising approach for more selective modulation of dopaminergic functions and consequently for successful therapeutic intervention in several abnormalities, such as schizophrenia, emotional or cognitive dysfunctions and addiction (see, e.g., Sokoloff, P. et al.: *Nature*, 1990, 347, 146; Schwartz, J. C., et al.: *Clin. Neuropharmacol.*, 1993, 16, 295; Levant, B.: *Pharmacol. Rev.*, 1997, 49, 231), addiction (see, e.g., Pilla, C. et al.: *Nature*, 1999, 400, 371) and Parkinson's disease (see, e.g., Levant, B. et al.: *CNS Drugs*, 1999, 12, 391) or pain (see, e.g., Levant, B. et al.: *Neurosci. Lett.* 2001, 303, 9).

The dopamine $D_2$ receptors are widely distributed in the brain and are known to be involved in numerous physiological functions and pathological states. $D_2$ antagonists are widely used drugs as antipsychotics, for example. However, it is also well known that massive antagonism of the $D_2$ receptors leads to unwanted side-effects such as extrapyramidal motor symptoms, psychomotor sedation or cognitive disturbances. These side effects seriously restrict the therapeutic utilization of $D_2$ antagonist compounds. (Wong A. H. C. et al.: *Neurosci. Biobehav. Rev.*, 2003, 27, 269).

In a further aspect, the present invention provides a method of treating conditions which require preferential modulation of dopamine $D_3$ and/or $D_2$ receptors, for example psychoses (e.g., schizophrenia, schizo-affective disorders), cognitive impairment accompanying schizophrenia, mild-to-moderate cognitive deficits, dementia, psychotic states associated with dementia, psychotic depression, mania, acute mania, bipolar disorder, paranoid and delusional disorders, dyskinetic disorders such as Parkinson's disease, neuroleptic induced parkinsonism, tardive dyskinesia, eating disorders (e.g., bulimia nervosa), attention deficit disorders, hyperactivity disorders in children, depression, anxiety, sexual dysfunction, sleep disorders, emesis, aggression, autism and drug abuse, which comprises administering to a subject in need thereof an effective amount of the co-crystal of the present invention.

A preferred use for $D_3/D_2$ antagonists with $D_3$ preference according to the present invention is in the treatment of schizophrenia, schizo-affective disorders, cognitive impairment accompanying schizophrenia, mild-to-moderate cognitive deficits, dementia, psychotic states associated with dementia, psychotic depression, mania, acute mania, bipolar disorder, bipolar depression, major depressive disorder, paranoid and delusional disorders, dyskinetic disorders such as Parkinson's disease, neuroleptic induced parkinsonism, depression, anxiety, drug abuse (e.g., cocaine abuse).

In one embodiment, the condition treated is schizophrenia. In another embodiment, the condition treated is acute mania. In a further embodiment, the condition treated is acute mania associated with bipolar disorder.

The particular combination of the two receptor-actions described above allows the simultaneous manifestation of the beneficial actions of both the $D_3$ antagonism (e.g., cognitive enhancer effect, inhibition of extrapyramidal motor symptoms, inhibitory action on drug abuse) and the $D_2$ antagonism (e.g., antipsychotic effect). Furthermore, the same combination surprisingly results in canceling out the disadvantageous features of $D_2$ antagonism (e.g., extrapyramidal symptoms, psychomotor sedation, cognitive disturbances).

In some embodiments, the co-crystals of the present invention are administered as a mono-therapy. In other embodiments, the co-crystals of the present invention are administered as part of a combination therapy. For example, =co-crystals of the invention may be used in combination with other drugs or therapies that are used in the treatment/prevention/suppression or amelioration of the diseases or conditions for which compounds of the invention are useful. Such other drug(s) may be administered, by a route and in an amount commonly used therefor, contemporaneously or sequentially with a compound of the invention. When co-crystals of the present invention is used contemporaneously with one or more other drugs, a pharmaceutical unit dosage form containing such other drugs in addition to the co-crystal of the invention may be employed. Accordingly, the pharmaceutical compositions of the present invention include those that also contain one or more other active ingredients, in addition to the co-crystals of invention.

Subjects suffering from and in need of treatment of, e.g., schizophrenia, acute mania, and other conditions mentioned above can be treated by the administering a therapeutically effective amount of co-crystalline trans-1{4-[2-[4-(2,3-dichlorophenyl)-piperazin-1-yl]-ethyl]-cyclohexyl}-3,3-dimethyl urea hydrochloride and an acid such as fumaric acid (optionally with one or more other form(s) or solvate of trans-1{4-[2-[4-(2,3-dichlorophenyl)-piperazin-1-yl]-ethyl]-cyclohexyl-}-3,3-dimethyl-urea hydrochloride, such as, for example, Form I and/or Form III of trans-1{4-[2-[4-(2,3-dichlorophenyl)-piperazin-1-yl]-ethyl]-cyclohexyl}-3,3-dimethyl-urea hydrochloride and/or trans-1{4-[2-[4-(2,3-dichlorophenyl)-piperazin-1-yl]-ethyl]-cyclohexyl}-3,3-dimethyl-urea hydrochloride formic acid solvate) formulated according to, for example and without limitation, the compositions and dosage forms described herein.

DEFINITIONS

The term "about" or "approximately" as used herein means within an acceptable error range for the particular value as determined by one of ordinary skill in the art, which will depend in part on how the value is measured or determined, i.e., the limitations of the measurement system. For example, "about" can mean within one or more than one standard deviations, per the practice in the art. Alternatively, "about" can mean a range of up to 20%, preferably up to 10%, more preferably up to 5%, and more preferably still up to 1% of a given value.

The term "pharmaceutically acceptable" means biologically or pharmacologically compatible for in vivo use in animals or humans, and preferably means approved by a regulatory agency of the Federal or a state government or listed in the U.S. Pharmacopeia or other generally recognized pharmacopeia for use in animals, and more particularly in humans.

The term "schizophrenia" is intended to include the group of mental disorders characterized by disruptions in thinking and perception, and includes schizophrenia (and all its subtypes; paranoid, catatonic, disorganized, residual, undifferentiated) and other psychotic disorders (as per Diagnostic and Statistical Manual for Mental Disorders, Fourth Edition. Washington, D.C. (1994): American Psychiatric Association, or The ICD-10 Classification of Mental and Behavioural Disorders: Clinical Descriptions and Diagnostic Guidelines, Geneva (1992): World Health Organization) such as schizophreniform and schizoaffective disorders, brief psychotic disorder, etc.

In a clinical evaluation, schizophrenia is commonly marked by "positive symptoms" such as hallucinations (especially auditory hallucination which are usually experienced as voices), disorganized thought processes and delusions as well as "negative symptoms" which include affective flattening, alogia, avolition, and anhedonia.

The term "the negative symptoms of schizophrenia" refer to a class of symptoms of schizophrenia which can be considered to reflect a "loss" in functional, directed thought or activity. Negative symptoms of schizophrenia are well known in the art, and include affective flattening (characterized by, for example, an immobile and/or unresponsive facial expression, poor eye contact and reduced body language), alogia ("poverty of speech" or brief, laconic and/or empty replies), avolition (characterized by a reduced or absent ability to initiate and carry out goal-directed activities), anhedonia (loss of interest or pleasure), asocialty (reduced social drive and interaction), apathy and other negative symptoms known to those of skill in the art. The negative symptoms of schizophrenia may be assessed using any methodology known in the art including, but not limited to, the Brief Psychiatric Rating Scale (BPRS), and the Positive and Negative Symptom Scale (PANSS). The BPRS and PANSS have subscales or factors that can be used to measure negative symptoms. Other scales have been designed to address specifically negative symptoms: For example the Scale for the Assessment of Negative Symptoms (SANS), the Negative Symptoms Assessment (NSA) and the Schedule for the Deficit Syndrome (SDS). Subscales of the BPRS and PANSS may also be used to assess positive symptoms, although methods for specifically assessing positive symptoms are also available (e.g., the Scale for the Assessment of Positive Symptoms, or SAPS).

The terms "cognitive impairment associated with schizophrenia" and "cognitive defects associated with schizophrenia" refers to cognitive deficits in schizophrenia patients. Cognitive impairment in schizophrenia is a core feature of the illness (i.e. not a result of treatment or clinical symptoms). Cognitive deficits include, but are not limited to deficits of attention/vigilance, working memory, verbal learning and memory, visuospatial memory, reasoning/problem solving and social cognition. There are numerous neuropsychological tests used to measure cognitive deficits in schizophrenia, such as the Wisconsin Card Sorting Test (WCST).

The term "substantially pure" means a compound having a purity greater then, e.g., about 90% by weight, for example, greater than about 91% by weight, greater than about 92% by weight, greater than about 93% by weight, greater than about 94% by weight, greater than about 95% by weight, greater than about 96% by weight, greater than about 97% by weight, greater than about 97.5% by weight, greater than about 98% by weight, greater than about 99% by weight, greater than about 99.5% by weight, or greater than about 99.9% by weight.

The terms "treat," "treatment," and "treating" refer to one or more of the following: to relieve, alleviate, delay, reduce, reverse, improve or prevent at least one symptom of a condition in a subject. The term "treating" may also mean to arrest, delay the onset (i.e., the period prior to clinical manifestation of a disease) and/or reduce the risk of developing or worsening a condition.

An "effective amount" means the amount of the co-crystals of the present invention that, when administered to a patient (e.g., a mammal) for treating a disease, is sufficient to effect such treatment for the disease, or an amount of a compound that is sufficient for modulating a dopamine receptor (e.g., the dopamine $D_2$ and/or dopamine $D_3$ receptor) to achieve the objectives of the invention. The "effective amount" will vary depending on the compound, the disease and its severity and the age, weight, etc., of the patient to be treated.

The term "therapeutically effective" applied to dose or amount refers to that quantity of a compound or pharmaceutical formulation that is sufficient to result in a desired activity upon administration to a mammal in need thereof. As used herein with respect to the pharmaceutical formulations comprising co-crystals of trans-1{4-[2-[4-(2,3-dichlorophenyl)-piperazin-1-yl]ethyl]-cyclohexyl}-3-,3-dimethyl-urea, the term "therapeutically effective amount/dose" refers to the amount/dose of the compound that, when combined, is sufficient to produce an effective response upon administration to a subject or patient.

A subject or patient in whom administration of the therapeutic compound is an effective therapeutic regimen for a disease or disorder is preferably a human, but can be any animal, including a laboratory animal in the context of a clinical trial or screening or activity experiment. Thus, as can be readily appreciated by one of ordinary skill in the art, the methods, compounds and compositions of the present invention are particularly suited to administration to any animal, particularly a mammal, and including, but not limited to, humans, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use.

The following examples are merely illustrative of the present invention and should not be construed as limiting the scope of the invention in any way as many variations and equivalents that are encompassed by the present invention will become apparent to those skilled in the art upon reading the present disclosure.

EXAMPLES

X-Ray Powder Diffraction (XRPD) Analysis

A small amount of sample (~12 mg) was placed on a zero background holder and exposed to CuKα radiation (30 kV×15 mA) in a Rigaku miniflex X-ray diffractometer (Danvers, Mass.). The angular range was 2° to 40° 2θ, and counts were accumulated at a continuous scan rate of 1°/mm. Data collection and analysis were performed using commercially available software (JADE, version 8.0, Materials Data, Inc., Livermore, Calif.).

Differential Scanning Calorimetry (DSC)

A differential scanning calorimeter (MDSC, Model Q1000, TA Instruments, Wilmington, Del.) with a refrigerated cooling accessory was used to acquire all DSC traces. A DSC cell was calibrated with pure samples of indium. Approximately 3-8 mg of co-crystal was weighed in an aluminum pan, hermetically sealed, and heated from 25-300° C. at 10° C./min heating rate under nitrogen flow (flow rate 50 mL/min).

Attenuated Total Reflectance Fourier Transform Infrared Spectroscopy (ATR-FTIR)

A Thermo-Nicolet Nexus-670 unit equipped with a DTGS detector (Thermo Instrument Co., Madison, Wis.) was used to acquire FTIR spectra. Samples (~5 mg) were placed under a zinc selenide (ZnSe) attenuated total reflectance (ATR) crystal accessory and a torque of ~20 cNm was applied to ensure full contact. 200 co-added scans were collected at a resolution of 2 $cm^{-1}$ within the region of 4000-600 $cm^1$.

Thermogravimetric Analysis (TGA)

A Thermogravimetric analyzer (Pyris 1, Perkin Elmer, Wellesley, Mass.) with air cooling was used. About 3-7 mg of sample was weighed in platinum TGA pans and heated under dry nitrogen purge (flow rate 70 mL/min) at 10° C./min. The data was analyzed using Pyris software (version 5.00.02, Perkin Elmer, Wellesley, Mass.).

General Experimental Procedure

Co-crystals of trans-1{4-[2-[4-(2,3-dichlorophenyl)-piperazin-1-yl]-ethyl]-cyclohexyl}-3,3-dimethyl urea hydrochloride and fumaric acid were prepared using a variety of solvents under the conditions below:

(i) A small amount of trans-1{4-[2-[4-(2,3-dichlorophenyl)-piperazin-1-yl]-ethyl]-cyclohexyl}-3,3-dimethyl urea hydrochloride Form I was first mixed with equal molar ratio of fumaric acid. A few drops of an organic solvent, for example, methanol or acetonitrile, were added to the mixture. The mixture was mechanically ground for about 5-15 minutes. After grinding, the sample was characterized by powder XRPD, DSC, TGA, FTIR and FT-Raman.

(ii) A 1:1 mixture of trans-1{4-[2-[4-(2,3-dichlorophenyl)-piperazin-1-yl]-ethyl]-cyclohexyl}-3,3-dimethyl urea hydrochloride and fumaric acid was added to 15 mL of an organic solvent, such as methanol. The solution was then slowly evaporated. After evaporation, the solids were collected and analyzed by powder XRPD, DSC, TGA, FTIR and FT-Raman.

Example 1

Preparation of Co-Crystal of Trans-1{4-[2-[4-(2,3-dichlorophenyl)-piperazin-1-yl]-ethyl]-cyclohexyl}-3,3-dimethyl urea hydrochloride and Fumaric Acid A co-crystal of trans-1{4-[2-[4-(2,3-dichlorophenyl)-piperazin-1-yl]-ethyl]-cyclohexyl}-3,3-dimethyl urea hydrochloride and fumaric acid was prepared using procedure ii) of the above general procedure, using methanol as the solvent.

Peak locations for the XRPD patterns in FIG. 1 are provided in Table 1 below.

TABLE 1

| 2θ (°) | d-spacing (Å) | Relative intensity |
|---|---|---|
| 8.31 | 10.633 | 11 |
| 11.06 | 7.994 | 2.7 |
| 12.33 | 7.171 | 2 |
| 12.53 | 7.060 | 2 |
| 12.88 | 6.870 | 1.5 |
| 14.49 | 6.107 | 13.2 |
| 15.58 | 5.682 | 9.5 |
| 16.39 | 5.406 | 4.4 |
| 16.69 | 5.307 | 3.9 |
| 17.13 | 5.173 | 20.7 |
| 17.33 | 5.113 | 12.3 |
| 17.80 | 4.979 | 7.6 |
| 18.00 | 4.923 | 6.1 |
| 18.18 | 4.877 | 13.2 |
| 18.80 | 4.716 | 32.3 |
| 20.35 | 4.361 | 1.2 |
| 20.69 | 4.290 | 20.8 |
| 21.10 | 4.207 | 7.7 |
| 22.24 | 3.994 | 100 |
| 22.56 | 3.938 | 6.6 |
| 22.90 | 3.880 | 13 |
| 23.23 | 3.826 | 3.5 |
| 23.49 | 3.784 | 5.8 |
| 23.81 | 3.734 | 1.8 |
| 24.11 | 3.688 | 4.1 |
| 24.35 | 3.653 | 2.2 |
| 24.67 | 3.606 | 7.9 |
| 25.20 | 3.531 | 17.3 |
| 25.72 | 3.461 | 24.2 |
| 26.10 | 3.411 | 6.9 |
| 26.56 | 3.354 | 47.6 |
| 26.97 | 3.304 | 27.6 |
| 27.43 | 3.249 | 2.5 |
| 28.56 | 3.123 | 2.5 |
| 28.88 | 3.089 | 10.3 |
| 29.18 | 3.058 | 9.8 |
| 29.53 | 3.023 | 21.6 |
| 29.88 | 2.988 | 5.5 |
| 30.33 | 2.944 | 25.5 |
| 30.96 | 2.886 | 2.9 |
| 31.38 | 2.848 | 13.4 |
| 31.69 | 2.822 | 20 |
| 32.21 | 2.777 | 4.4 |
| 33.67 | 2.664 | 18.6 |
| 34.30 | 2.613 | 27.6 |
| 34.54 | 2.595 | 10.1 |
| 34.96 | 2.564 | 4 |

TABLE 1-continued

| 2θ (°) | d-spacing (Å) | Relative intensity |
|---|---|---|
| 35.98 | 2.494 | 3.4 |
| 36.53 | 2.458 | 17.9 |
| 37.46 | 2.399 | 4.4 |
| 37.89 | 2.373 | 6.5 |
| 38.54 | 2.334 | 22.5 |
| 38.66 | 2.327 | 15.3 |
| 38.82 | 2.318 | 8.7 |
| 39.25 | 2.293 | 5.4 |
| 39.51 | 2.279 | 53.9 |

While this invention has been particularly shown and described with references to example embodiments thereof, it will be understood by those skilled in the art that the invention is not to be limited to particular details set forth in the above description. Various changes or modifications in form and details may be made therein without departing from the scope of the invention and are intended to be encompassed by the appended claims.

What is claimed is:

1. A co-crystal of trans-1{4-[2-[4-(2,3-dichlorophenyl)-piperazin-1-yl]-ethyl]-cyclohexyl}-3,3-dimethyl urea hydrochloride and fumaric acid having an X-ray powder diffraction pattern comprising characteristic peaks at about 8.3 and about 38.5±0.2 degrees 2θ.

2. The co-crystal of claim 1 having an X-ray powder diffraction pattern comprising characteristic peaks at about 8.3, about 36.5, about 38.5 and about 39.5±0.2 degrees 2θ.

3. The co-crystal of claim 1 having an X-ray powder diffraction pattern substantially as shown in FIG. 1.

4. The co-crystal of claim 1 having a melting endotherm at about 170° C. as determined by differential scanning calorimetry and a characteristic peak at about 8.3±0.2 degrees 2θ in an X-ray powder diffraction pattern.

5. A process for preparing a co-crystal of claim 1 comprising:
   (i) combining trans-1{4-[2-[4-(2,3-dichlorophenyl)-piperazin-1-yl]-ethyl]-cyclohexyl}-3,3-dimethyl urea hydrochloride, fumaric acid and an organic solvent to form a mixture, and
   (ii) grinding the mixture.

6. The process of claim 5, wherein the trans-1{4-[2-[4-(2,3-dichlorophenyl)-piperazin-1-yl]-ethyl]-cyclohexyl}-3,3-dimethyl urea hydrochloride and fumaric acid are present in a 1:1 ratio.

7. The process of claim 5, wherein the organic solvent is selected from the group consisting of tetrahydrofuran, methanol, acetonitrile, ethylacetate, acetone, chlorofoim, and a mixture thereof.

8. A process for preparing a co-crystal of claim 1 comprising:
   (i) adding trans-1{4-[2-[4-(2,3-dichlorophenyl)-piperazin-1-yl]-ethyl]-cyclohexyl}-3,3-dimethyl urea hydrochloride and fumaric acid to an organic solvent to form a mixture, and
   (ii) evaporating the organic solvent.

9. The process of claim 8, wherein the trans-1{4-[2-[4-(2,3-dichlorophenyl)-piperazin-1-yl]-ethyl]-cyclohexyl}-3,3-dimethyl urea hydrochloride and fumaric acid are present in a 1:1 ratio.

10. The process of claim 8, wherein the organic solvent is selected from the group consisting of tetrahydrofuran, methanol, acetonitrile, ethylacetate, acetone, chloroform, and a mixture thereof.

11. The process of claim 8, wherein step (ii) comprises evaporating the organic solvent at ambient pressure and temperature.

12. A pharmaceutical composition comprising a co-crystal of claim 1, and one or more pharmaceutically acceptable excipients.

* * * * *